United States Patent
Dawson (10) Patent No.: US 7,556,929 B2
(45) Date of Patent: Jul. 7, 2009

(54) COMPOSITIONS AND METHODS FOR SCREENING ANTI-CANCER AGENTS IN YEAST

(75) Inventor: Dean Dawson, Jamaica Plain, MA (US)

(73) Assignee: Tufts University, Boston, MA (US)

( * ) Notice: Subject to any disclaimer, the term of this patent is extended or adjusted under 35 U.S.C. 154(b) by 229 days.

(21) Appl. No.: 11/396,927

(22) Filed: Apr. 3, 2006

(65) Prior Publication Data
US 2006/0223101 A1 Oct. 5, 2006

Related U.S. Application Data

(60) Provisional application No. 60/668,444, filed on Apr. 5, 2005.

(51) Int. Cl.
*G01N 33/569* (2006.01)
*G01N 33/53* (2006.01)

(52) U.S. Cl. ............ 435/7.1; 435/244; 435/254.1; 435/254.2; 435/254.11; 435/463

(58) Field of Classification Search ............ 435/7.31, 435/244, 463, 254.2, 245.11, 254.1
See application file for complete search history.

(56) References Cited

U.S. PATENT DOCUMENTS

2002/0160403 A1* 10/2002 Seeley .................. 435/6

OTHER PUBLICATIONS

Taylor et al, The Jrnl. of Cell biology, 142(1), 1998, 1-11.*
Baker et al., 2004, Nat. Genet. 36:744-49.
Baudat et al., 2000, Mol. Cell 6:989-98.
Boeke et al., 1984, Mol. Gen. Genet. 197:345-46.
Boumil et al., 2003, Mol. Genet. Genomics 268:750-60.
Chan et al., 1999, J. Cell Biol. 146:941-54.
Cheslock et al., 2005, Nat. Genet. 37:756-60.
Gorbsky, 2001, Curr. Biol. 11:R1001-04.
Hassold et al., 2001, Nat. Rev. Genet. 2:280-91.
Hodges et al., 2002, Hum. Reprod. 17:1171-80.
Hoyt, 2001, J. Cell. Biol. 154:909-11.
Hoyt et al., 1991, Cell 66:507-517.
Hunt et al., 2002, Science 296:2181-83.
Jallepalli et al., 2001, Nature Rev. Cancer 1:109-17.
Kaback et al., 1992, Science 256:228-232.
Kamieniecki et al., 2000, Currrent Biol. 10:1182-90.
Kemp et al., 2004, Genes Dev. 18:1946-51.
Kong et al., 2004, Nat. Genet. 36:1203-06.
Lamb et al., 1996, Nat. Genet. 14:400-05.
Lemaire-Adkins et al., 1997, J. Cell Biol. 139:1611-19.
Lew et al., 2003, Annu. Rev. Genet. 37:251-82.
Li et al., 1991, Cell 66:519-31.
Li et al., 1996, Science 274:246-48.
Longtine et al., 1998, Yeast 14:953-61.
Meraldi et al., 2004, Dev. Cell. 7:45-60.
Mukherjeee et al, 2001, Curr. Med. Chem. 8:1467-86.
National Cancer Institute, 2002, Developmental Therapeutics Program [http://www.dtp.nci.nih.gov/branches/dscb/repo_open.html].
Nicolas et al., 1989, Nature 338:35-39.
Nicklas, 1997, Science 275:632-37.
Nicklas et al., 1969, J. Cell. Biol. 43:40-50.
Panvichian et al., 1999, Urology 54:746-52.
Ross et al., 1995, Genetics 142:79-89.
Shanks et al., 2001, Genetics 159:939-51.
Shonn et al., 2000, Science 289:300-03.
Shonn et al., 2003, Curr. Biol. 13:1979-84.
Steuerwald et al., 2001, Mol. Hum. Reprod. 7:49-55.
Trielli et al., 1996, J. Cell Biol. 135:689-700.
Volarcik et al., 1998, Hum. Reprod. 13:154-60.
Wang et al., 2000, Cancer 88:2619-28.
Wassmann et al., 2003, Curr. Biol. 13:1596-1608.
Yvon et al., 1999, Mol. Biol. Cell. 10:947-59.
Zhang et al., 2004, Biol. Reprod. 71:740-48.
Zhang et al., 2005, Biol. Reprod. 72:58-68.

* cited by examiner

*Primary Examiner*—T. D. Wessendorf
(74) *Attorney, Agent, or Firm*—Sonia K. Guterman; Lawson & Weitzen, LLP (57) ABSTRACT

Methods and kits for identifying novel anti-tumor agents are provided.

12 Claims, 4 Drawing Sheets

COMPOSITIONS AND METHODS FOR SCREENING ANTI-CANCER AGENTS IN YEAST

RELATED APPLICATION

The invention claims the benefit of U.S. provisional application having Ser. No. 60/668,444 filed Apr. 5, 2005, the entire contents of which are hereby incorporated herein by reference.

GOVERNMENT SUPPORT

The invention was supported in part by National Institutes of Health grant R01 GM63896. The government has certain rights in the invention.

FIELD OF THE INVENTION

Methods and kits for screening anti-cancer agents in yeast with human spindle checkpoint genes, spindle checkpoint mutations or aneuploid chromosome content are provided.

BACKGROUND

Breast cancer results from the accumulation of alterations to the genome, such as mutations, acquired or inherited, chromosomal re-arrangements, and deviations from the diploid chromosome number. Together, these genetic changes can allow cells to bypass cellular growth control mechanisms. One such mechanism is the spindle checkpoint. The proteins of the spindle checkpoint prevent progression of the cell into anaphase until all chromosomes are properly attached to microtubules. The spindle checkpoint is implicated in both the origins and treatment of breast cancer. Studies have failed to show any universal defect in the spindle checkpoint genes in breast tumors. Under-expression or defects in the spindle checkpoint genes can contribute to chromosome instability in tumors.

The spindle checkpoint is also important for the treatment of breast cancer. The anti-tumor drug, taxol, halts cell growth by altering microtubule dynamics in a way that activates the spindle checkpoint, resulting in cell cycle arrest, and ultimately, apoptotic cell death. Weakening of the spindle checkpoint may be one avenue to the resistance of tumor cells to taxol.

Breast cancer is thought to result from the accumulation of alterations to the genome, such as mutations, acquired or inherited, chromosomal re-arrangements, and deviations from the normal chromosome number. Such chromosomal changes defined as "aneuploid" compare to normal "euploid" chromosome arrangements and number. Together, these genetic changes allow the cancer cells to avoid the mechanisms that control cell growth.

One of the mechanisms used to control growth and retain the proper chromosome number in normal cells is called the spindle checkpoint. The spindle checkpoint is a surveillance mechanism that stops cells from undergoing what could be an errant division that would result in an inappropriate number of chromosomes in the daughter cells. The spindle checkpoint machinery is able to do this by monitoring the attachment of the chromosomes to the cellular cables (called microtubules) that pull the chromosomes into the two daughter cells. If a chromosome fails to attach to the cables, the spindle checkpoint machine produces a signal that blocks the cell division process. If the cell fails to fix the problem, the cell is usually programmed to die by apoptosis. While this might seem drastic, it is advantageous for the body to kill occasional "problem" cells rather than risk creating a cell with the wrong number of chromosomes, because having the wrong number of chromosomes can lead to a cell becoming a cancer cell.

In recent years, one of the most effective anti-breast cancer drugs has been taxol. Taxol causes a structural problem with the cables that pull chromosomes into daughter cells. As a consequence, the spindle checkpoint mechanism senses the problem with the attachment of the taxol-treated cables to the chromosomes, and prevents cell division. This results in cell death. Tumors that do not respond to taxol may have defects in the spindle checkpoint system, which prevent the defective spindle checkpoint from sensing the problems with the taxol-treated cables, so that the cells can avoid the arrest and death.

Novel anti-tumor agents are needed to treat tumors that do not respond to taxol or that do not respond to other anti-cancer agents, and to treat tumors that have acquired resistance to anti-cancer agents.

SUMMARY

In one embodiment, methods provided herein identify compounds that act on components of the spindle checkpoint to activate the checkpoint and trigger mitotic arrest, even in the absence of any insults to the microtubules or chromosomes. Such compounds have utility in analyzing the mechanisms of the spindle checkpoint, and more importantly, are developed to generate anti-cancer therapeutics. Compounds identified by the methods herein are envisioned that could potentiate, i.e., activate the spindle checkpoint might be used in conjunction with existing agents, such as taxol, that work by causing cell cycle arrest. Checkpoint potentiators could augment the taxol-generated arrest, making cancer cells more sensitive to taxol. If the agents identified herein, i.e., potentiators worked at the downstream portion of the spindle checkpoint mechanism they might mediate arrest by taxol in cells with upstream spindle checkpoint defects, which cells would normally escape taxol-induced arrest and apoptosis.

Thus the invention of the methods and kits provided herein is based on the mechanism that tumor cells evade anti-cancer compounds like taxol because they have a weak spindle checkpoint. Therefore it may be possible to block growth of these tumors by administering compounds identified as anti-cancer agents by their ability to activate spindle checkpoint proteins, causing these proteins to then arrest the cell cycle of the tumor cells. Such agents will arrest growth of a cell that contains the gene for that protein, but will not arrest the growth of a matched cell that does not contain that gene.

Accordingly, the invention in one embodiment provides a method of identifying a compound from a library of low molecular weight compounds that activates a spindle checkpoint protein, the method including: contacting with the at least one compound a sample of a first strain of cells and a sample of a second strain of cells, wherein cells of the first strain contain a gene encoding the protein and cells of the second strain lack a gene encoding the protein in a functional form; and observing arrest of growth of the first strain of cells in comparison to the second strain of cells, and in comparison to a second sample of the first strain of cells absent the compound, the strains grown under conditions that are otherwise identical to, wherein the compound activates the spindle checkpoint. In general, the cells are yeast cells such as *Saccharomyces*, for example, *S. cerevisiae*, or are *Kluyveromyces* species, however any eukaryotic cell capable of cell culture having a well developed genetic system is appropriate.

In certain embodiments, the cells of the first strain contain a wild type gene for each of the spindle checkpoint genes. In a related embodiment, the cells of the second strain contain a deletion in at least one spindle checkpoint gene. In a related embodiment, the first strain contains the deletion and further contains a replacement gene of human origin that complements function of the gene. In a related embodiment, the gene with the deletion is MAD3 and the replacement human gene is hBUBR1. In general, cells of the first and second strains are haploid. The mutation is selected from the group consisting of a deletion in a gene selected from the group of MAD1, MAD2, MAD, BUB1, and BUB3. It may be advantageous in certain embodiments to use a plurality of strains, i.e., a mixture of strains, such that at least one of the first strain or the second strain comprises a plurality of mutations, or comprises a mixture of cells having different genotypes.

It is generally recognized that more efficacious compositions exhibit activity at lower concentrations, however for an initial assay some arbitrary concentrations must be established, particularly for screening large numbers of compounds in a high throughput format. While the particular parameters of the screen can be varied by one of ordinary skill in the art in order to optimize conditions, and it is envisioned that in various embodiments the scope of the invention herein covers all of these parameters, in at least one embodiment, contacting further comprises the compound at a concentration of at least about 5 µM. However useful screens may use substantially lower concentrations for an initial assay, for example, 0.1 µM, 0.5 µM, 1, 2, or 3 µM as is understood by the artisan skilled in assay development. It may also be of use initially to use a higher concentration. In that scenario, contacting further comprises the compound at a concentration of at least about 50 µM, however other higher concentrations or intermediate concentrations are similarly useful and are within the scope of the invention. These specifications are useful for reproducibility and comparison purposes among different iterations of the screen using the same compounds, or different iterations of the screen using previously untested compounds, but the choice of a standard initial concentration for each screen is essentially arbitrary.

Further, according to an embodiment of the method, arresting growth is observing an optical density of cells of less than about 0.01, or less than about 0.05, or less than about 0.1. Similarly, observing growth is observing an optical density of cells of at least about 0.5, or at least about 1.0, or at least about 1.5, or at least about 2.0. In a related embodiment, the method further comprises determining a concentration of the agent that inhibits 50% of growth, i.e., the determining the parameter known as $IC_{50}$. Also provided is a method of determining reversibility of the effect of the agent, by removing the compound and observing a resumption in the growth of the arrested cells.

A related embodiment of the method is evaluating the phenotype of the arrested cells, for example, evaluating the phenotype is analyzing morphology of at least one of the nucleus and the spindles. In certain embodiments, evaluating the phenotype is determining a synergism with a microtubule-destabilizing agent. The microtubule-destabilizing agent can be a *Vinca* alkaloid such as Vinblastin or Vincristine; a taxol such as Paclitaxel (taxol) or Docetaxel (taxotere); a colchicine; and a nocodozole.

In another embodiment, methods herein are based on data that show that aneuploid cells have an enhanced dependence on the spindle checkpoint. Because cancer cells are frequently aneuploid whereas normal cells are not, this difference is exploited for development of tumor specific inhibitory compounds. Methods are provided that can identify compounds that specifically inhibit the growth of aneuploid cells. Such compounds would provide a starting point for development as anti-tumor compounds that block the growth of aneuploid cells.

Accordingly, also provided herein are screens for anti-tumor agents, these screens based on the mechanism that cells that are aneuploid, i.e., having an abnormal chromosomal number or arrangement or morphology may be more dependent on spindle checkpoint function than euploid cells having a normal chromosomal complement or karyotype. Accordingly in one embodiment is provided a method of screening a plurality of compounds to identify a compound that is an anti-tumor agent, the method comprising: contacting a sample of an aneuploid strain of cells having enhanced dependence on a spindle checkpoint with the at least one compound of the plurality; and observing inhibition of growth of the aneuploid cells in comparison to a control sample of the aneuploid cells in the absence of the compound, and in comparison to a euploid strain of cells, such that the comparison cells are grown under conditions that are otherwise identical (except for the absence of the agent), and the agent that compromises the spindle checkpoint of the aneuploid cells is identified as the anti-tumor composition. In general, the aneuploid strain and the euploid strain are yeast strains, for example, a *Saccharomyces*. In certain embodiments, the strains carry a deletion of a yeast spindle checkpoint protein and a replacement human gene encoding a spindle checkpoint protein, wherein the human gene complements the yeast deletion. In certain embodiments, the cells are diploid. For example, the aneuploid cell is a monosomic cell or a tetraploid cell.

In a related embodiment prior to contacting, the method further includes engineering the aneuploid cell to select for monosomy. Monosomic cells as used in the methods herein have one homolog of a chromosome selected from the group of chromosome I, chromosome III, and an exogenously transfected artificial chromosome, compared to diploid euploid cells which have two of each chromosome. In certain embodiments, the aneuploid strain and the euploid strain are otherwise isogenic.

Also provided herein is a kit for screening for an antitumor agent, comprising at least one yeast strain selected from the group of a strain having a deletion and a human replacement gene selected from the group of human genes consisting of MAD1, MAD2, MAD3, BUB1, BUBR1, and BUB3; at least one aneuploid strain; and a container and instructions for use with a plurality of compounds. Thus the kit can have one or more yeast strains selected from a group of strains, including the deletion strains, the deletion/replacement strains, and the aneuploid strains provided herein. In certain embodiments of the kit, the aneuploid strain is monosomic or tetraploid. The kit can include both a monosomic strain and a tetraploid strain.

BRIEF DESCRIPTION OF THE DRAWINGS

FIG. 1A shows that chiasmata, the cytological manifestations of recombination, work together with sister chromatid cohesion (ovals) to hold homologues together, beginning in prophase and continuing until cohesion is degraded in anaphase.

FIG. 1B shows that chiasmata promote proper segregation because the tension generated by spindle forces pulling in opposite directions on homologous kinetochores, stabilizes microtubule attachments ensuring a bipolar spindle attachment. Homologs that fail to recombine (the shorter chromosomes shown at the lower end of the figure) are more likely to segregate independently of each other, sometimes moving to the same pole at anaphase I (non-disjunction).

Single mutants with only exchange chromosomes (FIG. 2A) or with one non-exchange chromosome pair (FIG. 2B) were sporulated and ninety-six tetrads of each strain were dissected. Viability was judged via growth on medium YPD. (FIG. 2C) Single mutants with one non-exchange chromosome pair were sporulated and ninety-six tetrads of each strain were dissected. Chromosomes were labeled with selectable markers that made it possible to determine their segregation in meiosis by tetrad analysis. Cells were replica plated to selective media and chromosome segregation was scored by the presence or absence of commonly used auxotrophic markers. The chromosome I pair is a normal chromosome pair capable of recombination. The chromosome V pair recombines in less than one percent of cells (9). Exchange chromosome Strains: WT (DBK205), MAD1Δ (DBK223), MAD2Δ (DBK224), MAD3Δ (DBK225). Non-Exchange chromosome strains: WT (DBK203), MAD1Δ (DBK219), MAD2Δ (DBK220), MADΔ (DBK221), MAD3Δ+hBUBR1 (DPC32).

Isogenic strains (WT, MAD1Δ, MAD2Δ, or MAD3Δ) were induced to undergo a synchronous meiosis. Samples were removed periodically and evaluated using nuclear, spindle, and spindle pole body morphology to determine the percent of cells that had initiated and proceeded through either anaphase I (post anaphase I panels A and C) or prophase I (post prophase I panels B and D). In each panel the kinetics of four isogenic strains were compared, i.e., percent of cells in a particular phase (post-prophase I or post-anaphase I) on the ordinate as a function of time after induction, in hours, on the abscissa. All graphs reflect the average of multiple experiments. (A) Anaphase I entry, strains with a normal chromosome set. (B) Exit from prophase I, strains with a normal chromosome set. (C) Anaphase I entry, strains with one non-exchange chromosome pair. (D) Exit from prophase I, strains with one non-exchange chromosome pair. Exchange chromosome strains: WT (DPC12), MAD1Δ (DPC11), MAD2Δ (DPC10), MAD3Δ (DPC9). Non-Exchange chromosome strains: WT (DBK203), MAD1Δ (DBK219), MAD2Δ (DBK220), MAD3Δ (DBK221).

Mad3p acts in every meiotic cell to mediate a two-to-three hour delay in meiotic prophase. This delay occurs whether or not the cell contains an error-prone chromosome pair. The delay appears crucial for the segregation of non-exchange chromosomes. The MAD3 delay may provide time for the non-exchange chromosomes to achieve centromere pairing that mediates their segregation (16) or alternatively may provide time for the non-exchange pair to make important microtubule attachments. Mad1p and Mad2p can trigger a metaphase delay in response to a non-exchange chromosome pair. Mad1p and Mad2p delay the metaphase-to-anaphase transition about one hour at which time cells appear to enter anaphase even if the problem chromosomes have not achieved a bipolar spindle attachment.

DETAILED DESCRIPTION

The methods provided herein identify new chemical compounds that might be developed as candidate anti-cancer drugs. Our approach takes advantage of the fact that the proteins of the spindle checkpoint also exist in bakers yeast, *Saccharomyces cerevisiae*. In fact, the spindle checkpoint genes were discovered in experiments with yeast. To identify new drugs that might make taxol more effective, or might be used in place of taxol, we use yeast to find chemicals that interact with the spindle checkpoint mechanism, causing it to arrest cell growth. Whereas taxol does this indirectly by affecting the cables (microtubules), methods herein find chemicals that directly interact with the spindle checkpoint machine to cause it to transmit the "arrest growth" signal. Yeast cells rather than human cells are used because: it is possible to modify the genes in yeast such that they will give predictable growth patterns in the presence of the chemical we are seeking. This would be very difficult in human cells. It is possible to inexpensively and rapidly grow yeast in very small containers that allow us to test thousands of chemicals in a cost efficient way. The spindle checkpoint systems of humans and yeast are very similar. Therefore, a chemical that works in yeast can work in human cells, or can be used as a lead compound to develop derivatives that work in human cells.

Data herein further show specific killing of aneuploid cells with drugs that inactivate the spindle checkpoint system. Methods herein provide a search for chemical compounds that specifically arrest or kill cells, such as tumor cells, that carry an abnormal number of chromosomes.

An important development in the treatment of breast cancer in recent years has been use of drugs such as taxol that interact with microtubules in a way that ultimately causes cell death. In dividing transformed cells, taxol induces a mitotic arrest that usually culminates in apoptosis, whereas in non-transformed cells it induces a reversible G1 arrest (42). In tumor cells, taxol treatment triggers several signaling pathways in a concentration dependent manner. At low concentrations, like those likely to occur in therapeutic use, the arrest and subsequent apoptosis depend on the spindle checkpoint (44, reviewed in 43).

The spindle checkpoint mechanism was originally identified in yeast (32,11). The spindle checkpoint monitors attachment of microtubules to chromosomes, and proper orientation of chromosomes on the mitotic spindle. The mechanism of checkpoint function and the protein components are highly conserved (MAD1, MAD2, MAD3/BUBR1, BUB1, BUB3, MPS1; reviewed in (31). A kinetochore that has failed to become properly attached to microtubules produces a spindle checkpoint signal that blocks further progress of the cell cycle. The manner in which the spindle checkpoint produces the cell cycle arrest is an area of intense investigation.

A model is that either of two proteins Mad2p or BubR1p (or complexes including one of these proteins) can bind to and inactivate a protein, Cdc20p, whose action is necessary for activity of a ubiquitin ligase (termed the anaphase promoting complex, APC). Specific proteolytic degradation of cell cycle proteins by the APC (guided by active Cdc20p) is required to drive the cell from metaphase into anaphase.

Checkpoint signals may also modify the APC, for example by phosphorylation, making it "inhibitable" (reviewed in 30). In mammalian cells, this spindle checkpoint mediated arrest appears to lead to apoptosis under some conditions (38). At least a portion of the cellular Mad2p and Mad3/BubR1 reside at the kinetochore with other spindle checkpoint proteins where they are involved in monitoring microtubule attachment (23,36). Failure of the kinetochore to attach properly to microtubules is thought to allow the release of the forms of Mad2p and BubR1 that interact with Cdc20p causing the cell cycle delay. In wild-type yeast growing in standard laboratory medium, there is no need for the spindle checkpoint in most cell cycles and therefore spindle checkpoint mutants exhibit growth indistinguishable from wild-type cells. However, in the presence of certain agents or mutations that disrupt spindle function, the spindle checkpoint becomes essential, and spindle checkpoint mutants die because they are unable to delay passage into anaphase until all of their chromosomes have attached properly to the mitotic spindle (32,11).

Figure 1:
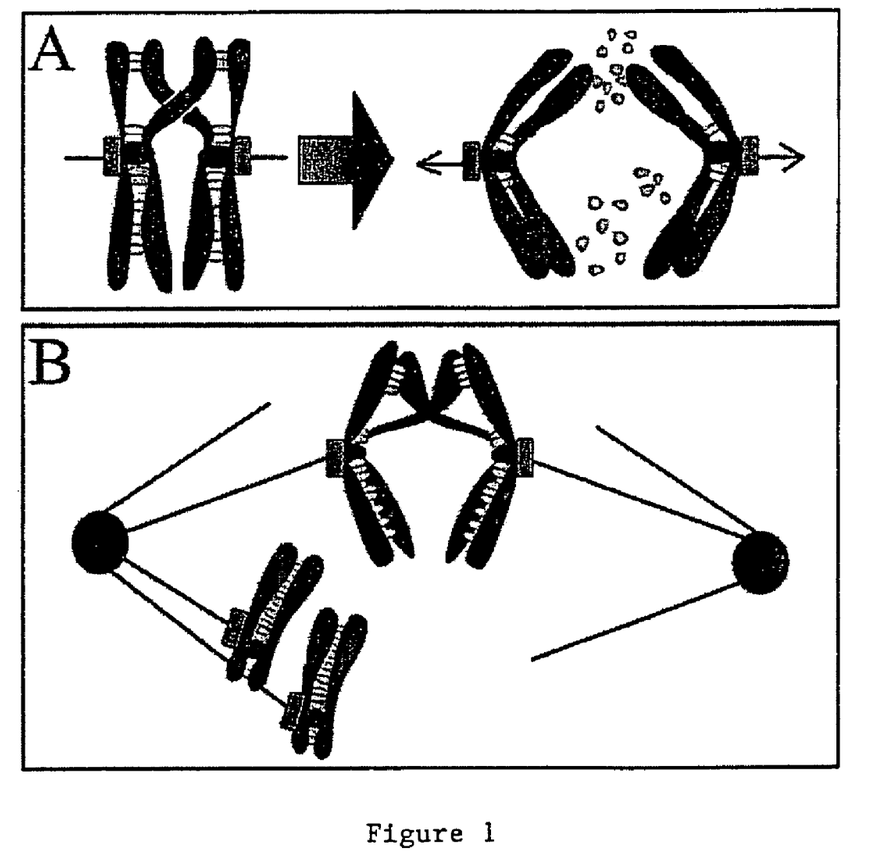
FIG. 1 is a set of drawings showing recombination and chromosome segregation in meiosis.

Errors in human meiotic chromosome segregation are the leading cause of spontaneous abortions and birth defects (1). In many organisms, including humans, meiotic crossovers (exchanges) between homologous chromosomes ensure their proper segregation. Homologous chromosomes that fail to experience exchanges are error-prone, more likely than exchange chromosomes to be segregated incorrectly in meiosis (FIG. 1). We have employed a yeast model to investigate the mechanisms used to partition such "error-prone" chromosomes. These studies demonstrate differential roles in meiosis for the spindle checkpoint genes MAD1, MAD2 and MAD3. Our experiments reveal a novel meiotic role for MAD3; while largely dispensable for the segregation of exchange chromosomes MAD3 is essential for the proper meiotic segregation of error-prone non-exchange chromosomes. In the absence of MAD3 function, non-exchange chromosomes segregate randomly in meiosis I. While MAD1 and MAD2 act in a surveillance mechanism that mediates a metaphase delay in response to non-exchange chromosomes, MAD3 mediates a delay before metaphase, in every meiosis, apparently acting as a crucial meiotic timer. The meiotic role of MAD3 in non-exchange chromosome segregation in yeast could be fulfilled by a human homolog, hBUBR1. These findings have important implications for the basis of errant meiotic segregation in humans.

We developed a yeast model system to explore the molecular mechanisms that usually ensure proper meiotic chromosome segregation (9). Normally all of the chromosome pairs in a yeast cell experience one or more exchanges during meiosis (10). We have engineered a strain that carries one non-exchange chromosome pair (chromosome V) in virtually every meiosis (9). Thus, these cells mimic the situation in oocytes that have suffered the "first hit" (4). Cells bearing this non-exchange pair were used to explore the role of the spindle checkpoint genes MAD1, MAD2, and MAD3 in the meiotic segregation of error-prone chromosomes. Previous studies have shown that the spindle checkpoint genes are important for segregation fidelity in a variety of organisms, and studies in yeast have demonstrated that meiotic exchange chromosomes are much more dependent upon the spindle checkpoint for proper segregation than are mitotic chromosomes (11-13).

Without being limited by any particular theory as to the mechanism of action, the present invention is based on theories regarding particular observations from examples presented herein. The first is that compounds that interact with spindle checkpoint proteins in a way that causes these proteins to assume an "active" form trigger a cell cycle arrest in the absence of any actual problems with microtubules or kinetochores. The second is that aneuploid cells have a requirement, not seen in euploid cells, for a functional spindle checkpoint, and are thereby vulnerable to compounds that interact with and possibly inhibit the spindle checkpoint.

Examples herein identify compounds that activate spindle checkpoint proteins using high throughput screens of small compound libraries against genetically modified yeast strains. Other examples herein involve generating yeast strains that carry human spindle checkpoint genes and screening for compounds specific for the human spindle checkpoint proteins. Examples herein further test aneuploid cells for an elevated dependence on the spindle checkpoint, then identify compounds that preferentially inhibit the growth of aneuploid cells.

Examples herein are performed using yeast as a model organism, exploiting the conservation of the spindle checkpoint mechanism between yeast and mammalian cells. Standard yeast molecular genetic methods will be used for constructing the yeast strains and replacing yeast genes with their human cognates. Screening of small compounds, i.e., libraries having a plurality of organic molecules of low molecular weight, is done in a 384 well format using pin transfer devices to inoculate cultures and add small compounds. Induction of cell cycle arrests is monitored by failure of wild type strains to grow in the presence of drugs that do not inhibit cells deleted for spindle checkpoint genes. A goal will be to identify compounds that arrest growth of wild-type cells but do not inhibit the growth of cells lacking a spindle checkpoint.

Small compounds identified can be developed to identify drugs that augment the action of taxol or work alone to induce cell cycle arrest of tumor cells. Compounds identified may lead to the development of drugs that specifically block the growth of aneuploid cells and therefore may have high specificity for tumor cells as opposed to normal cells.

Innovations herein are powerful screening platforms that will identify compounds with important activities. The screen for potentiating compounds will identify chemical families that can be developed as anti-tumor compounds that increase the efficacy of existing drugs that work through the spindle checkpoint. This is particularly true if we are able to complement, i.e., substitute, the yeast spindle checkpoint genes with their human homologs. Observations herein of a dependence of monosomic strains on the spindle checkpoint is the first experimental evidence that the aneuploidy of tumor cells may really be exploited as a therapeutic target. Development of our observations in yeast will reveal the molecular foundations of the phenomenon sufficiently to facilitate its analysis in mammalian cells. Successful identification in these screens of compounds with full or partial phenotypes would encourage future screens of more extensive small compound libraries, the chemical diversification and re-testing of the most encouraging compounds, and the transition to mammalian cell-based screens modeled on those described here.

Some of the invention is based on a manuscript entitled, "The Roles of MAD1, MAD2, and MAD3 in Meiotic Progression and the Segregation of Non-Exchange Chromosomes" by Peter S. Cheslock, Benedict J. Kemp, Rebecca M. Boumil and Dean S. Dawson, published in Nature Genetics Vol. 37 pp. 756-760, Jun. 12, 2005, and which is entirely incorporated herein by reference.

EXAMPLES

The following Materials and Methods are used throughout the Examples below.

Strains and Culture Conditions.

Standard media and methods were used for these experiments (25). All strains were derived from S288C progenitors (26). All strain genotypes are listed in Table 1.

TABLE 1

Strains

| Strain | Genotype | Chromosome V |
|---|---|---|
| TB105 | MATa, leu2-3, 112, lys2-ΔB, his3-Δ1, arg4-ΔHpa, cup1::ura3::THR3, ilv1-Kpn, PAC2::[pD174: LEU2 lacO] | S. carlsbergensis |
| TBK109 | MATα, ade1::ARG4, leu2-3, 112, ura3::HIS3: Pr$_{CYC}$-GFP-lacI], PAC2::[pD174: LEU2 lacO], trp2, his3-11, 15, arg4-ΔHpa, rad3, cyh2-1, ilv1-92, cup1::ura3::THR1 | S. cerevisiae |
| TBK203 | MATα, ade1::ARG4, leu2-3, 112, ura3::HIS3: Pr$_{CYC}$-GFP-lacI], PAC2::[pD174: LEU2 lacO], trp2, his3-11, 15, arg4-ΔHpa, rad3, cyh2-1, ilv1-92, cup1::ura3::THR1, mad1Δ::KAN | S. cerevisiae |
| TBK204 | MATa, leu2-3, 112, lys2-ΔB, his3-Δ1, arg4-ΔHpa, cup1::ura3::THR3, ilv1-Kpn, PAC2::[pD174: LEU2 lacO], mad1Δ::KAN | S. carlsbergensis |
| TBK205 | MATα, ade1::ARG4, leu2-3, 112, ura3::HIS3: Pr$_{CYC}$-GFP-lacI], PAC2::[pD174: LEU2 lacO], trp2, his3-11, 15, arg4-ΔHpa, rad3, cyh2-1, ilv1-92, cup1::ura3::THR1, mad2Δ::KAN | S. cerevisia |
| TBK206 | MATa, leu2-3, 112, lys2-ΔB, his3-Δ1, arg4-ΔHpa, cup1::ura3::THR3, ilv1-Kpn, PAC2::[pD174: LEU2 lacO], mad2Δ::KAN | S. carlsbergensis |
| TBK207 | MATα, ade1::ARG4, leu2-3, 112, ura3::HIS3: Pr$_{CYC}$-GFP-lacI], PAC2::[pD174: LEU2 lacO], trp2, his3-11, 15, arg4-ΔHpa, rad3, cyh2-1, ilv1-92, cup1::ura3::THR1, mad3Δ::KAN | S. cerevisiae |
| TBK208 | MATa, leu2-3, 112, lys2-ΔB, his3-Δ1, arg4-ΔHpa, cup1::ura3::THR3, ilv1-Kpn, PAC2::[pD174: LEU2 lacO], mad3Δ::KAN | S. carlsbergensis |
| DBK203.4B | MATα, ade1::ARG4, leu2-3, 112, ura3::HIS3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1 | S. cerevisiae |
| DBK203.32D | MATa, leu2-3, 112, ura3::HIS3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1 | S. cerevisiae |
| TBK210 | MATα, ade1::ARG4, leu2-3, 112, ura3::URA3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1, mad2Δ::KAN | S. cerevisiae |
| TBK211 | MATa, leu2-3, 112, ura3::HIS3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1, mad2Δ::KAN | S. cerevisiae |
| TBK212 | MATα, ade1::ARG4, leu2-3, 112, ura3::URA3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1, mad3Δ::KAN | S. cerevisiae |
| TBK213 | MATa, leu2-3, 112, ura3::HIS3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1, mad3Δ::KAN | S. cerevisiae |
| TBK214 | MATα, ade1::ARG4, leu2-3, 112, ura3::URA3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1, mad1Δ::KAN | S. cerevisiae |
| TBK215 | MATa, leu2-3, 112, ura3::HIS3: Pr$_{CYC}$-GFP-lacI], PAC2::[pD174: LEU2 lacO], trp2, his3Δ1, arg4-ΔHpa, rad3, cyh2-1, ilv1-92, cup1::ura3::THR1, mad1Δ::KAN | S. cerevisiae |
| TPC7 | MATa, his3-Δ200, ura3-Δ0, mad3Δ::NAT | S. cerevisiae |
| TPC8 | MATa, his3-Δ200, ura3-Δ0, mad2Δ::NAT | S. cerevisiae |
| TPC9 | MATa, his3-Δ200, ura3-Δ0, mad1Δ::NAT | S. cerevisiae |
| BY4723 | MATa, his3-Δ200, ura3-Δ0 | S. cerevisiae |
| DPC31.28d | MATa, leu2-3, 112::[pPC4: Pr$_{MAD3}$ hBubR1 LEU2], his3-Δ1, ura3-52, trp1-289. arg4-Δ57RV-, mad3Δ::KAN | S. carlsbergensis |
| DBK203 | DBK105 X DBK109 | S. cerevisiae/ S. carlsbergensis |
| DBK219 | DBK203 X DBK204 | S. cerevisiae/ S. carlsbergensis |
| DBK220 | DBK205 X DBK206 | S. cerevisiae |
| DBK221 | DBK207 X DBK208 | S. cerevisiae/ S. carlsbergensis |
| DBK205 | DBK203.4B X DBK203.32D | S. cerevisiae |

TABLE 1-continued

Strains

| Strain | Genotype | Chromosome V |
|---|---|---|
| DBK223 | TBK214 X TBK215 | S. cerevisiae |
| DBK224 | TBK210 X TBK211 | S. cerevisiae |
| DBK225 | TBK212 X TBK213 | S. cerevisiae |
| DPC9 | TBK207 X TPC7 | S. cerevisiae |
| DPC10 | TBK205 X TPC8 | S. cerevisiae |
| DPC11 | TBK203 X TPC9 | S. cerevisiae |
| DPC12 | BY4723 X TBK109 | S. cerevisiae |
| DPC32 | DPC31.28D X TBK207 | S. cerevisiae/ S. carlsbergensis |

Genetic Manipulation of Yeast.

Construction of gene knockouts was accomplished using methods of Longtine and colleagues (27). All MAD mutations are complete deletions of the open reading frame. Chromosome segregation of both the exchange and non-exchange pairs was determined by tetrad analysis and growth on selective media as previously described (9).

Construction of the Non-Exchange Pair.

This strain was constructed by replacing one copy of S. cerevisiae chromosome V with chromosome V from Saccharomyces carlsbergensis, which provides full function in haploid S. cerevisiae. A detailed account of the creation and evaluation of this strain has been previously described (9).

Meiotic Time Course.

Diploid cells were induced to undergo synchronous sporulation as follows: Cultures grown overnight in YPD were used to inoculate flasks containing YPAcetate. These were grown overnight at 30° to an approximate density of $5 \times 10^7$ cells per ml. Sporulation was induced by transfer to 1% potassium acetate at a density of $5 \times 10^7$ cells per ml, and incubated with vigorous shaking (200 rpm) at 30°. Transfer to potassium acetate was considered to be T=0. Cells were harvested at the times indicated and fixed in 5% formaldehyde for 2 hours.

Microscopy.

Fixed cells were washed, spheroplasted and stained using previously described methods. To monitor spindle morphology, cells were incubated with rat anti-tubulin primary antibody (1:100) overnight at 4°. Subsequently, cells were washed and further incubated with Fluorescein (FITC)-conjugated donkey anti-rat IgG (1:100). Cells were washed and stained with 4'-6-Diamidino-2-phenylindole (DAPI) stained to visualize DNA. To monitor spindle pole body morphology, cells were incubated with rabbit anti-Tub4p (1:500) for 2-hours at room temperature. Subsequently cells were washed and further incubated with FITC-conjugated goat anti-rabbit IgG (1:500) for 1 hour at room temperature. Cells were washed and DAPI stained to visualize DNA. Samples were observed using an Olympus 100×1.4 numerical aperture objective lens. Images were collected and processed using a Hamamatsu Orca CCD and Openlab 3.0 software.

Example 1

Impact of MAD1, 2 or 3 Deletions on Normal Chromosomes

Spore viability was used to determine the impact of MAD1, 2, or 3 deletions on strains carrying either a normal (all exchange) chromosome set or a strain carrying the error-prone pair. Proper meiotic chromosome segregation during sporulation yields four viable spores, held together in a structure called a tetrad. A meiosis I non-disjunction, a common segregation error of non-exchange chromosomes (FIG. 1), results in tetrads with only two viable spores. As described previously, when strains with only exchange chromosomes were used in this assay, loss of either Mad1p or Mad2p resulted in a decrease in spore viability, but cells lacking Mad3p exhibited spore viability indistinguishable from wild-type cells (FIG. 2A) (12,13).

Example 2

Impact of Deletions on a Non-Exchange Chromosome

Figure 2:
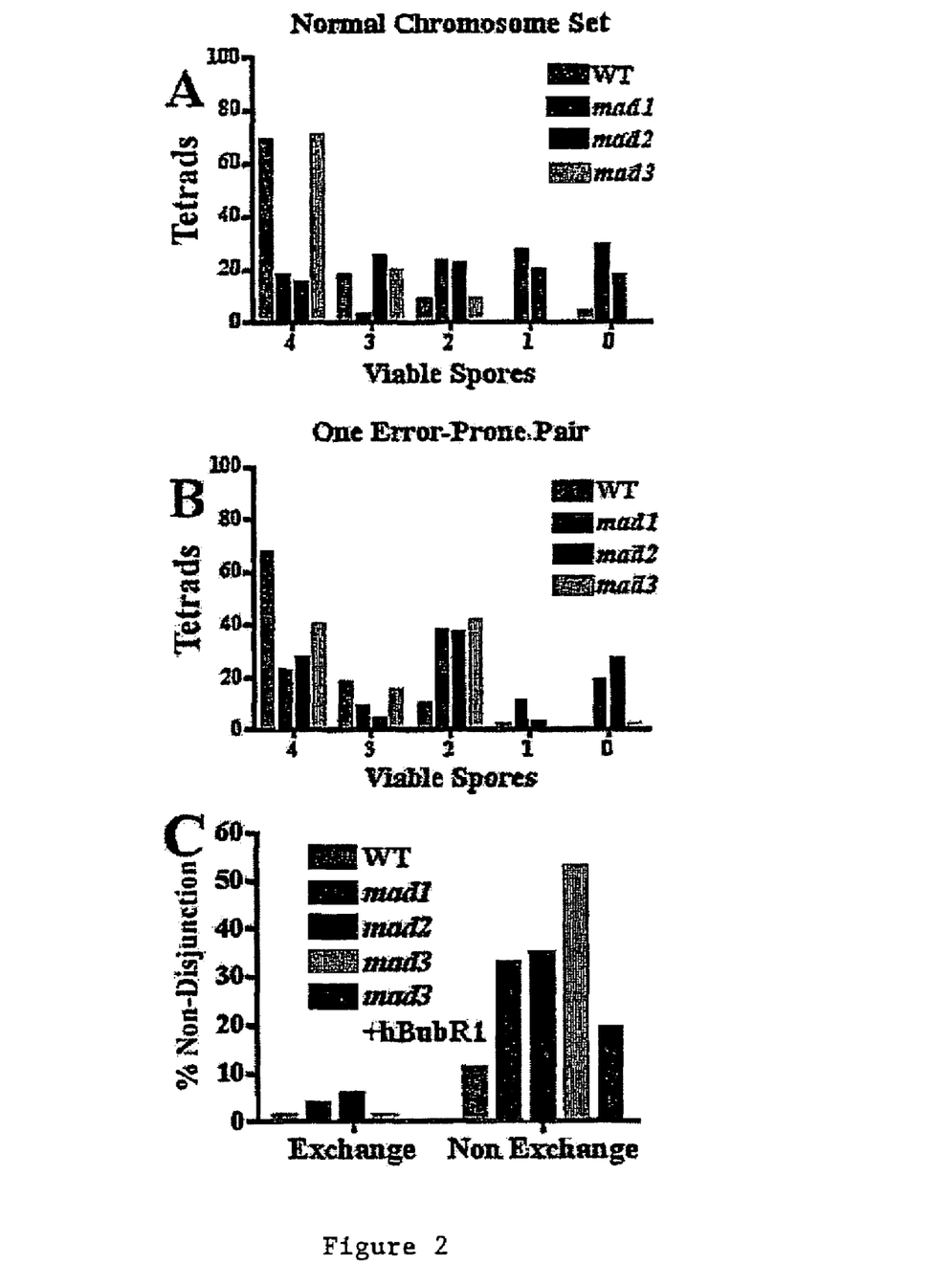
FIG. 2 is a set of bar graphs showing that Mad3p is crucial for the segregation of non-exchange chromosomes.

When cells bearing the non-exchange pair were evaluated, similar results were obtained, except in these strains the loss of Mad3p resulted in a decrease in spore viability (FIG. 2B). Thus, cells with a non-exchange chromosome pair are especially dependent on Mad3p. The increase in the two spore viable tetrads seen in the MAD3Δ mutant is consistent with meiosis I non-disjunction of a single chromosome pair.

The non-disjunction of both exchange chromosomes and the non-exchange pair was measured. The behavior of these chromosomes was evaluated in cells lacking individual spindle checkpoint genes. Data show that in this and other examples, loss of Mad1p or Mad2p resulted in 5-20% non-disjunction per exchange chromosome pair (FIG. 2C) (11-13).

Loss of Mad3p resulted in very small increases in non-disjunction frequencies of exchange pairs (FIG. 2C). In strains carrying a non-exchange pair, loss of either Mad1p or Mad2p resulted in a large increase in mis-segregation of the non-exchange pair (from 7% to ~25%; FIG. 2C), while loss of Mad3p resulted in completely randomized segregation of the non-exchange pair (50%; FIG. 2C).

These results demonstrate that non-exchange chromosomes are highly dependent upon a functional spindle checkpoint, and that Mad3p is crucial for their proper segregation.

Example 3

Role of Yeast MAD Genes in Cell Cycle Progression

In many instances the spindle checkpoint contributes to segregation fidelity by delaying the metaphase-to-anaphase transition in response to chromosome/spindle-related problems (11,12,14). But strains lacking Mad1p and Mad2p displayed differential behavior of meiotic chromosomes compared to strains lacking Mad3p in our assays, therefore we tested whether these genes had differential roles in controlling cell cycle progression in meiosis I.

Figure 3:
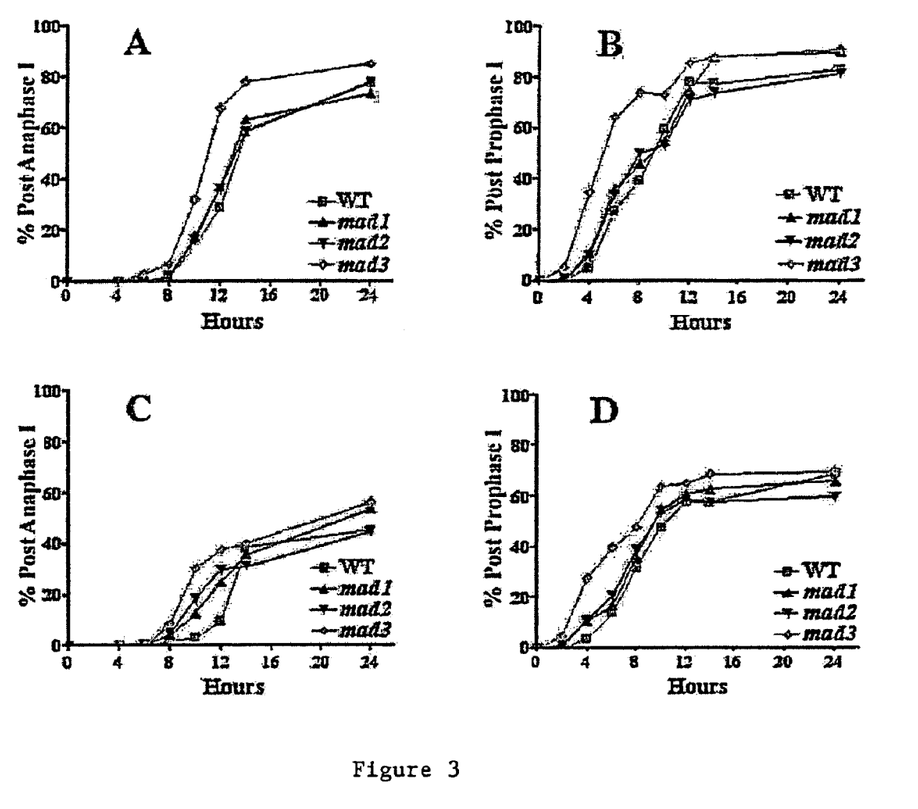
FIG. 3 is a set of line graphs showing that Mad3p imposes a delay in passage through meiosis I.

Initially, we monitored the timing of entry into anaphase I for isogenic strains that lack one of the MAD genes and carry only exchange chromosomes. In this example, wild-type cells and those lacking either Mad1p or Mad2p showed very similar or even indistinguishable kinetics (FIG. 3A). Although cells lacking Mad1p or Mad2p proceeded through the meiotic cell cycle with the same kinetics as wild-type cells, these cells show high levels of aneuploidy (FIG. 2A), demonstrating that in most meioses Mad1p and Mad2p act to rectify potentially errant segregation.

Mad1p and Mad2p can delay the metaphase-to-anaphase transition in the face of catastrophic insults to spindle/chromosome interactions (12,14), yet such delays were not detected in our assay (the WT strain was not delayed compared to the MAD1Δ and MAD2Δ strains). Thus, normal Mad1p/Mad2p mediated meiotic delays are brief in S. cerevisiae, and the correction of improper of inappropriate microtubule attachments must be rapid. Cells lacking Mad3p reached anaphase I two-to-three hours earlier than wild-type cells (FIG. 3A).

It is observed herein that in MAD3Δ strains, all of the chromosomes segregate correctly even without the Mad3p-mediated delay (FIG. 2A). Without being limited by any particular theory or mechanism of action, these data suggest that: 1) Mad3p acts in every meiosis to mediate a delay, and 2) the delay is not triggered by a potentially errant chromosome that requires the delay for its segregation. These findings are consistent with the recent observation that in mitotic mammalian cells a Mad3p homologue (BUBR1) mediates a delay in every cell cycle that is independent of kinetochore function (15).

Example 4

Mad3p Delay is Imposed in Prophase

Data herein suggest Mad3p might trigger a delay earlier than the spindle checkpoint metaphase-to-anaphase delay. First, data herein show that non-exchange chromosome partners segregate from each other very early in metaphase (16) and thus might not be able to benefit from a metaphase-to-anaphase delay. Second, the association between non-exchange partners is established in prophase, suggesting that a delay in this period of meiosis might benefit non-exchange segregation.

Therefore, the kinetics of the prophase I-to-metaphase I transition in isogenic wild-type and MADΔ strains carrying only exchange chromosomes was tested. We found that wild-type, MAD1Δ, and MAD2Δ strains behaved very similarly or even indistinguishably, however, MAD3Δ mutants exit prophase I about two-to-three hours earlier than the other strains (FIG. 3B). Thus the delay imposed by Mad3p is presumably in prophase I.

Example 5

Mad1p and Mad2p Impose Delay on Non-exchange Chromosomes

In cells bearing only exchange chromosomes, Mad1p and Mad2p are essential for allowing a crucial attachment or re-orientation of a chromosome pair that would otherwise non-disjoin (12,13). But any delay provided by Mad1p and Mad2p is undetectable (FIG. 3A). To test if Mad1p and Mad2p can induce a prolonged meiotic delay or arrest in cells with microtubule/chromosome problem that cannot be rectified, we repeated the time course assay in cells that contain one error-prone chromosome pair. Kinetochores experience tension upon bipolar spindle attachment and this tension stabilizes microtubule/kinetochore interactions. In meiosis, the linkage between homologous partners that is provided by exchanges is essential for creating the required tension (FIG. 1; 17,18). Thus the non-exchange pair should be unable to achieve the stable microtubule attachments required to satisfy the spindle checkpoint.

In this example, wild-type cells were found to reproducibly enter anaphase I about one hour later than MAD1 and MAD2 mutants, demonstrating that Mad1p and Mad2p mediate a one-hour delay in response to the non-exchange pair (FIG. 3C). The non-exchange pair mis-segregates in many wild-type cells demonstrating that Mad1p and Mad2p do not permanently arrest the cell cycle until the problem is corrected. Instead, these proteins trigger a delay after which the cell enters anaphase I, even if some chromosomes still are not properly oriented. Similar behavior is seen in mammalian oocytes, which utilize the spindle checkpoint to enhance meiotic segregation fidelity (19-21) but do not exhibit prolonged delays in response to errant chromosomes (22).

Example 6

Stage of Mad1p/Mad2p-Mediated Delay

To determine more precisely the stage at which the Mad1p/Mad2p-mediated delay occurs, we assayed the timing of entry into metaphase I for cells with an error-prone chromosome pair. Once again the MAD1, and MAD2 strains behaved very similarly or even indistinguishably from wild-type (FIG. 3D). This, coupled with the early entry into anaphase I of the MAD1Δ, and MAD2Δ versions of these strains (FIG. 3C), demonstrates that the Mad1/Mad2p-mediated delay is primarily in metaphase I.

Figure 4:
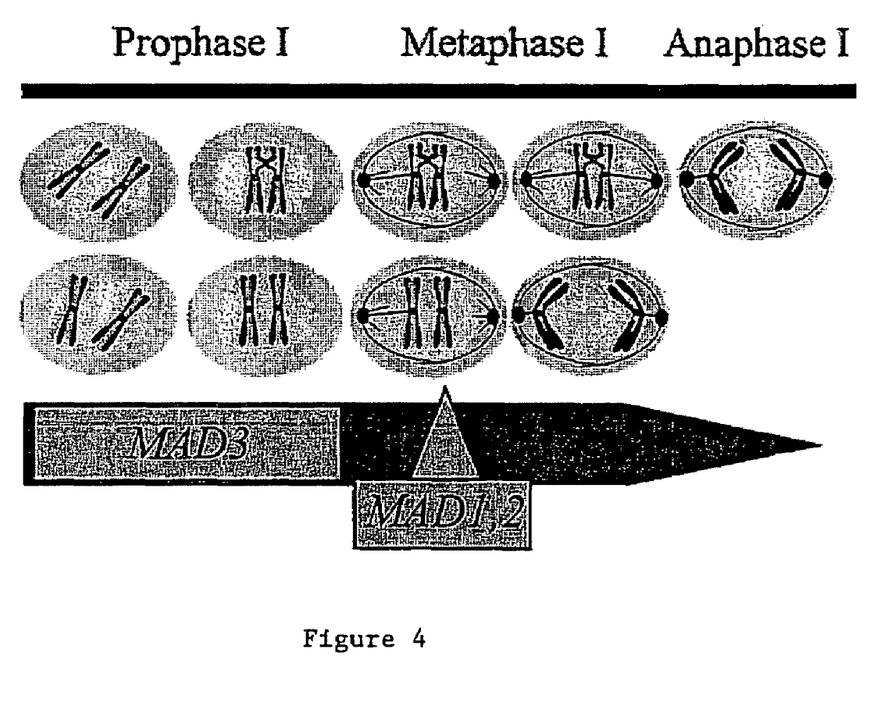
FIG. 4 is a drawing showing a model for timing of Mad1p, Mad2p, and Mad3p mediated delays.

These examples have examined the role of the spindle checkpoint genes in the segregation of error-prone chromosomes. The data herein show that Mad3p mediates a delay in each meiotic prophase, regardless of the presence of a potentially errant chromosome pair (FIG. 4). This delay is important for the segregation fidelity of chromosome pairs that have failed to recombine.

In addition, Mad1p and Mad2p trigger a delay in metaphase in response to errant chromosome pairs (FIG. 4), but this delay is not as effective as the Mad3p-mediated delay in ensuring proper disjunction. Without being limited to any particular theory or mechanism of action, it is likely that the delays provide either time for the establishment of pairing between the non-exchange partners (16), or additional time to attach to microtubules.

Example 7

Evaluation of Effect of Human Gene hBUBR1 Data

Examples herein show that failure of either recombination, or the MAD genes, renders chromosome segregation error-prone, while in most meioses chromosomes still segregate correctly. However, loss of both recombination and a MAD gene causes a randomization of meiotic segregation. The two-hit loss of meiotic segregation fidelity in yeast parallels the proposed basis of maternal age-related aneuploidies in humans. This similarity prompted us to test whether the mammalian homolog of MAD3, BUBR1 (23), might act as a functional homolog of MAD3 in yeast meiosis.

Non-disjunction of error-prone chromosomes in strains in which MAD3 was replaced by hBUBR1 was evaluated. The data show that hBUBR1 was able to rescue the mis-segregation defect exhibited in cells lacking Mad3p (FIG. 2C) consistent with the notion that BUBR1 may provide a critical function in human meiosis that is similar to the role of MAD3 in yeast. Recent experiments suggest that that the expression of hMAD2 and BUBR1 may be down regulated as a function of age in mammalian ovaries (6,24). These observations, coupled with our demonstration key roles for these genes in controlling the segregation of exchange, and especially non-exchange, chromosomes in meiosis, suggests that loss of spindle checkpoint function may contribute significantly to maternal age-related aneuploidy in humans.

Example 8

Phenotype of Mutants

A variety of methodologies are used to analyze the segregation behavior of chromosomes in yeast, primarily during meiosis. Based on data herein regarding the roles of the spindle checkpoint, we examined the spindle checkpoint as an anti-tumor therapeutic target. Though spindle checkpoint mutants have rather similar phenotypes in vegetative cells, they have dramatically different phenotypes in meiotic chromosome segregation assays (Table 2). These observations provide assays that distinguish MAD1/MAD2, from MAD3 from BUB1.

Example 9

Behavior of Aneuploid Cells

Diploid cells carrying only a single copy of one chromosome (monosomy) have an elevated dependence on certain spindle checkpoint genes. We have designed a strain that allows us to select for diploid cells that have lost one copy of chromosome III. We have built wild-type and MAD1/MAD1, MAD2/MAD2 and MAD3/MAD3 versions of this strain. To our surprise, we found that while isolating chromosome III monosomic strains in wild-type and MAD3/MAD3 diploids cells is straightforward, we were unable to isolate MAD1/MAD1 or MAD2/MAD2 strains that are monosomic for chromosome III (Table 3).

TABLE 2

Spindle checkpoint meiotic phenotypes

| Genotype | Meiotic phenotype |
| --- | --- |
| MAD1/MAD2 | mis-segregation of crossover or non-crossover homologs |
| MAD3 | missegregation only of non-crossover homologous |
| BUB1 | meiosis arrest |
| BUB3 | in progress |

TABLE 3

Frequency of monosomic cells

| Genotype | Monosomic Frequency |
| --- | --- |
| wild-type | $10^{-5}$ |
| MAD3 | $10^{-5}$ |
| MAD1 or MAD2 | $<10^{-7}$ |

This example shows that the combination of monosomy and loss of either MAD1 or MAD2 is synthetically lethal. As diploid cells perform a centromere pairing step in meiosis (35), one possibility is that this process is found in diploid mitotic cells. Because this preliminary finding has important implications for the treatment of tumors, experiments that clarify the underlying basis the apparent synthetic lethality of certain spindle checkpoint defects and monosomy are designed.

It is possible to isolate compounds that act directly on the proteins of the spindle checkpoint mechanism to render the checkpoint active and arrest cell growth. Examples provided herein enable search for spindle checkpoint-potentiating compounds as those that arrest the growth of wild-type cells but do not inhibit cells without the target spindle checkpoint genes.

Aneuploid cells are especially dependent on the spindle checkpoint for aligning their chromosomes on the spindle and in the absence of the spindle checkpoint are especially vulnerable to chromosome loss and therefore cell death. Aneuploid strains are not expected to yield "loop-outs" of modified spindle checkpoint loci that leave behind mutant spindle checkpoint genes, whereas wild-type cells will yield viable "loop-out" cells. Further, small compounds that inactivate systems used to help cells deal with aneuploidy will inhibit aneuploid cells but will not inhibit isogenic wild-type cells.

Example 10

Identification of Compounds that Potentiate Spindle Checkpoint Proteins

The experimental goal of this example is to take advantage of the genetic tractability of yeast to produce a chemical compound screening platform that will enable identifying compounds that cause the spindle checkpoint to become active, not because these compounds cause spindle damage, but rather because they induce key spindle checkpoint proteins to assume or mimic the active state.

Chemical compounds can disrupt or enhance biological processes at the protein level in a number of ways. Small molecules can enhance protein/protein interactions, disrupt protein/protein interactions, block active sites of enzymes or alter protein function by binding to a protein in a way that mimics a modification (a phosphorylation for example) (reviewed in 37,41). There exist many potential modes by which a small molecule could potentiate the spindle checkpoint. For example, interaction of a small molecule with a spindle checkpoint protein might enhance its interaction with Cdc20p, mimic a modification that renders the spindle protein "active", or enable it to interact with the APC in a manner that the renders it inhibitable.

The initial screen takes advantage of the fact that strains deleted for MAD1, MAD2, MAD3, BUB1 or BUB3 grow well mitotically in normal growth medium. However, in the presence of agents that disrupt spindle/kinetochore interactions, these mutants are vulnerable and die. A compound that acted directly with one of these gene products to trigger a spindle checkpoint arrest would arrest a wild-type strain. However, a strain deleted for the checkpoint gene would grow well in the presence of the compound, because in the absence of the target checkpoint protein there would be no way for the compound to induce the checkpoint arrest.

Standard molecular genetic techniques (25) are used to construct six isogenic haploid strains; one wild-type, and five strains bearing single deletions of MAD1, MAD2, MAD3, BUB1 or BUB3.

The strains described above are screened with a set of about 3000 compounds available from the National Cancer Institute for those that arrest (or partially arrest) the growth of wild-type cells but do not do so with one or more of the spindle checkpoint mutants. The NCI compound libraries to be screened are the Diversity Set (1990 compounds), the Mechanistic Set (879 compounds) and the Challenge Set (57 compounds; 33). These compounds have been selected from extensive small molecule libraries for their diversity of structure, and broad range of inhibitory patterns when tested against mammalian cell lines. The chemical sets are packaged in 384 well dishes at roughly equivalent concentrations (~10 mM).

The six strains are screened twice; once using a compound concentration of 5 µM and once at a concentration of 50 µM. In each screen, 384 well trays are seeded with 50 microliters/well of a growing yeast culture at $1 \times 10^5$ cells per ml ($OD_{660}$=0.01). Compounds are added to the wells using hand-held 384 pin transfer devices (V&P Scientific) calibrated to transfer nanoliter quantities of DMSO solutions. The 384 well trays are incubated at 30° C. for two days then screened for cell growth with a 384 well plate spectrophotometer. The initial screens search for compounds that significantly inhibit the growth of the wild-type strains (no growth, $OD_{660}$=0.01) but do not inhibit one or more strains with deleted spindle checkpoint genes (saturation growth, $OD_{660}$ of >2.0). Compounds with the reverse effect (those that kill or inhibit spindle checkpoint mutants but do not kill wild-type cells) are well known and should be evident in the screen, but compounds with the phenotype sought herein are not previously described. Many interesting compounds might yield intermediate phenotypes in the initial screens. Secondary screens (below) are used to determine whether these are acting by activating the spindle checkpoint.

Example 11

Secondary Screens to Characterize Candidate Compounds

Compounds that give the desired phenotype are further examined. We will be especially interested in two categories of compounds. Compounds with no growth defects in those spindle checkpoint mutants that grow in the presence of the compound are particularly interesting. Compounds that completely arrest wild type cells and also retard the growth of spindle checkpoint mutants may act on the kinetochores or microtubules in a way that activates the checkpoint in wild type cells (causing the arrest) but don't cause sufficient damage to kill spindle checkpoint mutants that proceed through the cell cycle in the presence of the damage (similar to low doses of nocodozole and MAD mutants, (11). Second, we focus on compounds whose arrest is bypassed by only a subset of the spindle checkpoint genes, as these are more likely to act specifically to trigger the checkpoint arrest. The compounds that produce the most desired results in the primary screen are subjected to a series of tests, including determining the $IC_{50}$ in wild-type cells and spindle checkpoint mutants; determining whether arrested wild-type cells are incurring irreversible damage as a result of treatment with the compound or alternatively can resume growth (the ideal expected phenotype); evaluating the arrest phenotype caused by the drug (nuclear and spindle morphologies) using our standard laboratory cell biology protocols (28,40); and determining whether the compound synergistically triggers a checkpoint arrest in low doses of a microtubule-destabilizing agent (such as nocodozole).

Eaxmple 12

Screen for Potentiators of Human Spindle Checkpoint Genes with the Yeast Screening Platform Over 100 yeast genes have been demonstrated to be complemented by their human homologs. Given the high homology between the yeast spindle checkpoint proteins and their human homologs, it is likely that some of the yeast spindle checkpoint proteins can be replaced by their human homologs. In cases where it is possible to do this, it provides a means to use the simple efficient methods used to grow and screen yeast cells for the analysis of mammalian protein function. We will test whether MAD1, MAD2, BUBR1, BUB1 or BUB3 from humans can replace the cognate yeast gene.

Conventional molecular genetic methods will be used (25) to replace open reading frames of the yeast spindle checkpoint genes with their human homologs. Further, strains bearing the human spindle checkpoint gene replacements are screened for their ability to complement the appropriate yeast spindle checkpoint mutant. Screens determine complementation of the inability of the yeast spindle checkpoint mutants to grow on low levels of the microtubule de-stabilizing compound nocodozole, and the different meiotic phenotypes we have found for MAD1, MAD2, MAD3 and BUB1 mutants (Table 3). Failure of any of the human genes to complement may be due to incompatibility of the interactions between the yeast and human spindle checkpoint proteins. In this eventuality pairwise complementation with human genes is attempted. Further, it may be possible to complement with individual domains of the human genes.

Strains that use a human protein as part of the spindle checkpoint mechanism are used to screen for compounds that arrest the growth of these strains but do not arrest cell growth when the cell is missing the function provided by the human gene. For example, the response of a strain complemented by human BUB1 with the BUB1 deletion strain is analyzed. A compound that arrests the growth of the complemented strain but not the BUB1 deletion strain is a candidate for a compound that "activates" the spindle checkpoint arrest through human Bub1p. The compound screens are performed as described above. The advantage to screening with the human-complemented strains is that it may identify compounds that interact with the human proteins but because of sequence divergence at the protein level do not interact with the yeast versions. Candidate compounds identified in these screens are subjected to the same secondary analyses as described above. These experiments test the theory that there are compounds able to activate the spindle checkpoint, independently of microtubule/kinetochore disruption.

Example 13

Identification of Compounds that Block Growth of Aneuploid Cells

Aneuploid cells are tested for dependence on the spindle checkpoint. The requirement of monosomic strains for functional spindle checkpoint genes is tested, and other types of aneuploidies are tested as follows. Standard genetic approaches (28,39,40) are used to monitor the dependence of monosomic strains on the spindle checkpoint genes. In the case of MAD1, diploid strains deleted for MAD1 on one chromosome and carrying a duplicated MAD1 locus on the other are constructed. One of the duplicated MAD1 genes bears a 200 base pair mutation including the start codon that renders the gene non-functional. Between the duplicated MAD1 genes a URA3 gene is inserted. This diploid strain carries one marked copy of chromosome III that allows us to select for cells that have lost it (which occurs in about one in 10,000 cells).

Both the original diploid and monosomic derivatives will be subjected to a fluctuation analysis, which reveals whether there is a growth disadvantage for monosome/MAD1 double mutants. Briefly, the diploid and monosomic strains are grown in rich medium then plated on 5-fluoro-orotic acid, which selects for URA3 mutants (29). Most URA cells result from a "loop-out" recombination between the duplicated MAD1 genes, leaving behind either the wild-type or the mutant version. In the diploid strain the loop-out should leave behind the MAD1 and MAD1Δ200 alleles at approximately equal frequencies (the identity of the residual allele will be determined by diagnostic PCR). If the monosome with the MAD1Δ200 mutation is synthetically-lethal, then loop-outs that leave this allele in the chromosome will not yield colonies (and PCR analysis will show that all FOA resistant monosomic colonies carry the MAD1 allele). If the combination is detrimental but not lethal, the monosome/MAD1Δ200 combination will give small colonies, whereas the monosome/MAD1 combination will give normal colonies. This same test is done with MAD2, MAD3 (which is not synthetically lethal with monosomy in our preliminary experiments), BUB1 and BUB2.

Methods used previously to build diploid strains that are monosomic for a different chromosome (chromosome I) are used to determine whether the affect is chromosome specific. Additionally, strains with an artificial chromosome that serves as a non-essential monosome and strains that have either three or four copies of a particular chromosome are constructed. These strains are used to test (as described above) whether previously observed dependence of monosomic III strains on the spindle checkpoint, extends to other chromosomes and types of aneuploidies.

Example 14

The Basis of Monosome Dependence on the Spindle Checkpoint

Whether centromere pairing is important in diploid mitosis and is the basis for monosome dependence on the spindle checkpoint is tested. We recently demonstrated that the aberrant behavior of a monosomic chromosome in meiosis is suppressed by adding a plasmid, bearing a centromere, to the cell. The centromere of the plasmid (CEN) appears to pair with the centromere of the monosome and in doing so helps confer normal meiosis I centromere behavior of the monosome. We test herein whether a CEN plasmid relieves the monosome/spindle checkpoint dependence. We further test whether imposing a cell cycle delay on the monosomic strain can substitute for the spindle checkpoint. This method (for example with the replication inhibitor, hydroxyurea) has been used to show that the role of the spindle checkpoint is primarily to provide a delay so that a retarded cellular process can be completed before the metaphase/anaphase transition (11). If hydroxyurea bypasses the requirement of monosomes for the spindle checkpoint this suggests that the monosomes are slow to attach to the microtubules.

Example 15

Screen Compounds that Arrest Growth of Aneuploid Strains

Because aneuploidy is a feature that distinguishes many tumor cells from wild-type cells this may be a desirable target for the development of anti-tumor therapeutics (34). Here we search for compounds that preferentially inhibit the growth of aneuploid cells as opposed to euploid cells, regardless of the target of the compound. We screen small compound libraries to identify compounds that inhibit the growth of an aneuploid strain but are less inhibitory to an isogenic euploid strain. Compounds identified in this screen will be tested to determine their inhibitory concentrations on both wild-type and aneuploid cells and their affects on wild-type cells suffering other cellular insults (nocodozole or DNA damage) that call for functional spindle checkpoints.

These experiments show that aneuploid cells are more dependent on the spindle checkpoint than euploid cells and enable identification of compounds that specifically block the growth of aneuploid cells.

REFERENCES

1. Hassold, T. & Hunt, P. To err (meiotically) is human: the genesis of human aneuploidy. *Nat Rev Genet* 2, 280-91 (2001).
2. Hunt, P. A. & Hassold, T. J. Sex matters in meiosis. *Science* 296, 2181-3 (2002).
3. Baudat, F., Manova, K., Yuen, J. P., Jasin, M. & Keeney, S. Chromosome synapsis defects and sexually dimorphic meiotic progression in mice lacking Spo11. *Mol Cell* 6, 989-98 (2000).
4. Lamb, N. E. et al. Susceptible chiasmate configurations of chromosome 21 predispose to non-disjunction in both maternal meiosis I and meiosis II. *Nat. Genet.* 14, 400-405 (1996).
5. Volarcik, K. et al. The meiotic competence of in-vitro matured human oocytes is influenced by donor age: evidence that folliculogenesis is compromised in the reproductively aged ovary. *Hum Reprod* 13, 154-60 (1998).
6. Steuerwald, N., Cohen, J., Herrera, R. J., Sandalinas, M. & Brenner, C. A. Association between spindle assembly checkpoint expression and maternal age in human oocytes. *Mol Hum Reprod* 7, 49-55 (2001).
7. Hodges, C. A. et al. Experimental evidence that changes in oocyte growth influence meiotic chromosome segregation. *Hum Reprod* 17, 1171-80 (2002).
8. Kong, A. et al. Recombination rate and reproductive success in humans. *Nat Genet* 36, 1203-6 (2004).
9. Boumil, R. M., Kemp, B., Angelichio, M., Nilsson-Tillgren, T. & Dawson, D. S. Meiotic segregation of a homeologous chromosome pair. *Mol Genet Genomics* 268, 750-60 (2003).
10. Kaback, D. B., Guacci, V., Barber, D. & Mahon, J. W. Chromosome size-dependent control of meiotic recombination. *Science* 256, 228-232 (1992).
11. Li, R. & Murray, A. W. Feedback control of mitosis in budding yeast. *Cell* 66, 519-531 (1991).
12. Shonn, M. A., McCarroll, R. & Murray, A. W. Requirement of the spindle checkpoint for proper chromosome segregation in budding yeast meiosis. *Science* 289, 300-3 (2000).

13. Shonn, M. A., Murray, A. L. & Murray, A. W. Spindle checkpoint component Mad2 contributes to biorientation of homologous chromosomes. *Curr Biol* 13, 1979-84 (2003).
14. Lew, D. J. & Burke, D. J. The spindle assembly and spindle position checkpoints. *Annu Rev Genet* 37, 251-82 (2003).
15. Meraldi, P., Draviam, V. M. & Sorger, P. K. Timing and checkpoints in the regulation of mitotic progression. *Dev Cell* 7, 45-60 (2004).
16. Kemp, B., Boumil, R. M., Stewart, M. N. & Dawson, D. S. A role for centromere pairing in meiotic chromosome segregation. *Genes Dev* 18, 1946-51 (2004).
17. Nicklas, R. B. & Koch, C. A. Chromosome manipulation III. Spindle fiber tension and the re-orientation of mal-oriented chromosomes. *J. Cell Biol.* 43, 40-50 (1969).
18. Nicklas, R. B. How cells get the right chromosomes. *Science* 275, 632-7 (1997).
19. Wassmann, K., Niault, T. & Maro, B. Metaphase I arrest upon activation of the Mad2-dependent spindle checkpoint in mouse oocytes. *Curr Biol* 13, 1596-608 (2003).
20. Zhang, D. et al. Intra-oocyte localization of MAD2 and its relationship with kinetochores, microtubules, and chromosomes in rat oocytes during meiosis. *Biol Reprod* 71, 740-8 (2004).
21. Zhang, D. et al. Localization of Mitotic Arrest Deficient 1 (MAD1) in Mouse Oocytes During the First Meiosis and Its Functions as a Spindle Checkpoint Protein. *Biol Reprod* 72, 58-68 (2005).
22. LeMaire-Adkins, R., Radke, K. & Hunt, P. A. Lack of checkpoint control at the metaphase/anaphase transition: a mechanism of meiotic nondisjunction in mammalian females. *J Cell Biol* 139, 1611-9 (1997).
23. Chan, G. K., Jablonski, S. A., Sudakin, V., Hittle, J. C. & Yen, T. J. Human BUBR1 is a mitotic checkpoint kinase that monitors CENP-E functions at kinetochores and binds the cyclosome/APC. *J Cell Biol* 146, 941-54 (1999).
24. Baker, D. J. et al. BubR1 insufficiency causes early onset of aging-associated phenotypes and infertility in mice. *Nat Genet* 36, 744-9 (2004).
25. Burke, D., Dawson, D. & Stearns, T. *Methods in yeast genetics: A Cold Spring Harbor Laboratory Course Manuel.* (Cold Spring Harbor Laboratory Press, Cold Spring Harbor, 2000).
26. Nicolas, A., Treco, D., Schultes, N. P. & Szostak, J. W. An initiation site for meiotic gene conversion in the yeast *Saccharomyces cerevisiae. Nature* 338, 35-39 (1989).
27. Longtine, M. S. et al. Additional modules for versatile and economical PCR-based gene deletion and modification in *Saccharomyces cerevisiae. Yeast* 14, 953-61 (1998).
28. Kamieniecki, R. J., Shanks, R. M. Q. & Dawson, D. S. Slk19p is necessary to prevent separation of sister chromatids in meiosis I. *Current Biol.* 10, 1182-1190 (2000).
29. Boeke, J. D., F. Lacroute, and G. R. Fink. A positive selection for mutants lacking orotidine-5'-phosphate decarboxylase activity in yeast. Mol. Gen. Genet. 197, 345-346 (1984).
30. Gorbsky, G. J. The mitotic spindle checkpoint. *Curr Biol* 11, R1001-4 (2001).
31. Hoyt, M. A. A new view of the spindle checkpoint. J Cell Biol 154, 909-11 (2001).
32. Hoyt, M. A., L. Totis, and B. Tibor Roberts. *S. cerevisiae* genes required for cell cycle arrest in response to loss of microtuble function. Cell 66, 507-517 (1991).
33. National Cancer Institue. Developmental Therapeutics Program. [http://www.dtp.nci.nih.gov/branches/dscb/repo_open.html] (2002).
34. Jallepalli, P. V., and C. Lengauer. Chromosome segregation and cancer: cutting through the mystery. Nature Rev Cancer 1, 109-17 (2001).
35. Kemp, B., R. M. Boumil, and D. S. Dawson. Non-exchange chromosome segregation in yeast is mediated by centromere pairing. Submitted (2002).
36. Li, Y., and R. Benezra. Identification of a human mitotic checkpoint gene: hsMAD2. Science 274, 246-8 (1996).
37. Mukherjee, A. K., S. Basu, N. Sarkar, and A. C. Ghosh. Advances in cancer therapy with plant based natural products. Curr Med Chem 8, 1467-86 (2001).
38. Panvichian, R., K. Orth, M. J. Pilat, M. L. Day, K. C. Day, C. Yee, J. M. Kamradt, and K. J. Pienta. Signaling network of paclitaxel-induced apoptosis in the LNCaP prostate cancer cell line. Urology 54, 746-52 (1999).
39. Ross, L. O., S. Rankin, M. Flatters, and D. Dawson. Effects of homology, size and exchange on the meiotic segregation of model chromosomes in *Saccharomyces cerevisiae.* Genetics 142, 79-89 (1996).
40. Shanks, R. M. Q., C. A. Bascom-Slack, and D. S. Dawson. The Kar3p-interacting proteins Cik1p and Vik1p have different roles in yeast meiosis. Genetics 159, 939-951 (2000).
41. Susa, M. Heterotrimeric G proteins as fluoride targets in bone (review). Int J Mol Med 3, 115-26 (1999).
42. Trielli, M. O., P. R. Andreassen, F. B. Lacroix, and R. L. Margolis. Differential Taxol-dependent arrest of transformed and nontransformed cells in the G1 phase of the cell cycle, and specific-related mortality of transformed cells. J Cell Biol 135, 689-700 (1996).
43. Wang, T. H., H. S. Wang, and Y. K. Soong. Paclitaxel-induced cell death: where the cell cycle and apoptosis come together. Cancer 88, 2619-28 (2000).
44. Yvon, A. M., P. Wadsworth, and M. A. Jordan. Taxol suppresses dynamics of individual microtubules in living human tumor cells. Mol Biol Cell 10, 947-59 (1999).

What is claimed is:

1. A method of identifying a compound from a library of low molecular weight compounds that activates a spindle checkpoint protein in haploid yeast cells, the method comprising:

contacting at least one compound from the library with a sample of a first strain of haploid yeast cells having a deleted yeast gene encoding the open reading frame of a yeast spindle checkpoint protein and containing a human homolog gene encoding the spindle checkpoint protein that complements the function of the cognate deleted yeast gene; and contacting the at least one compound with a sample of a second strain of haploid yeast cells also having the deleted yeast gene encoding the spindle checkpoint protein, the second strain not containing the human gene, wherein the yeast gene encoding the spindle checkpoint protein deleted in the first and second strains is selected from the group consisting of MAD1, MAD2, MAD3, BUB1, BUBR1 and BUB3;

observing arrest of growth of cells of the first strain in comparison to observing growth of cells of the second yeast strain, and in comparison to observing growth of cells of a second sample of the first strain absent the at least one compound and under conditions that are otherwise identical, wherein the compound that activates the spindle checkpoint in the first sample of the first strain is identified by observing arrest of growth of the first sample of the first strain contacted with the compound, in comparison to observing growth of the second strain contacted with the compound, and in comparison to observing growth in the second sample of the first strain of yeast cells absent the compound; and confirming that the compound activates the spindle checkpoint protein and arrests growth of cells by evaluating a phenotype of arrested cells, wherein evaluating the phenotype is analyzing morphology of at least one of the nucleus and the spindles of the arrested cells, thereby identifying the compound from a library of low molecular weight compounds that activates the spindle checkpoint protein.

2. The method according to claim 1, wherein the yeast gene deleted in the first and second strains is MAD3 and the human gene is hBUBR1.

3. The method according to claim 1, wherein contacting comprises the at least one compound at a concentration of at least 5 µM.

4. The method according to claim 1, wherein contacting comprises the at least one compound at a concentration of at least 50 µM.

5. The method according to claim 1, wherein arresting growth is observing an optical density of cells of less than about 0.01.

6. The method according to claim 1, wherein arresting growth is observing an optical density of cells of less than about 0.05.

7. The method according to claim 1, wherein arresting growth is observing an optical density of cells of less than about 0.1.

8. The method according to claim 1, wherein arresting growth is observing an optical density of cells of at least about 0.5.

9. The method according to claim 1, wherein arresting growth is observing an optical density of cells of at least about 1.0.

10. The method according to claim 1, wherein arresting growth is observing an optical density of cells of at least about 1.5.

11. The method according to claim 1, further comprising determining a concentration that inhibits 50% of growth.

12. The method according to claim 1, further comprising removing the compound and observing a resumption in the growth of the arrested cells.

* * * * *